US009488650B2

(12) United States Patent
Alocilja et al.

(10) Patent No.: US 9,488,650 B2
(45) Date of Patent: Nov. 8, 2016

(54) DETECTION OF CONDUCTIVE POLYMER-LABELED ANALYTES

(71) Applicant: BOARD OF TRUSTEES OF MICHIGAN STATE UNIVERSITY, East Lansing, MI (US)

(72) Inventors: Evangelyn C. Alocilja, East Lansing, MI (US); Emma Setterington, Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 0 days.

(21) Appl. No.: 14/480,162

(22) Filed: Sep. 8, 2014

(65) Prior Publication Data

US 2014/0377772 A1    Dec. 25, 2014

Related U.S. Application Data

(62) Division of application No. 13/477,205, filed on May 22, 2012, now Pat. No. 8,859,297.

(60) Provisional application No. 61/519,442, filed on May 23, 2011.

(51) Int. Cl.
*G01N 27/74* (2006.01)
*G01N 33/543* (2006.01)
*G01N 33/569* (2006.01)
*B82Y 15/00* (2011.01)
*H01F 1/00* (2006.01)

(52) U.S. Cl.
CPC ......... *G01N 33/56916* (2013.01); *B82Y 15/00* (2013.01); *G01N 27/745* (2013.01); *G01N 33/54326* (2013.01); *G01N 33/54333* (2013.01); *G01N 33/56911* (2013.01); *G01N 33/56983* (2013.01); *H01F 1/0054* (2013.01); *G01N 2333/245* (2013.01)

(58) Field of Classification Search
None
See application file for complete search history.

(56) References Cited

U.S. PATENT DOCUMENTS 4,486,530 A    12/1984   David et al.
4,786,589 A    11/1988   Rounds
4,939,096 A     7/1990   Tonelli
(Continued)

OTHER PUBLICATIONS

Conti, M. et al., "Capillary isoelectric focusing: the problem of protein solubility", Journal of Chromatography A (1997) 757:237-245.*

(Continued)

*Primary Examiner* — Mark Shibuya
*Assistant Examiner* — Gary E Hollinden
(74) *Attorney, Agent, or Firm* — Marshall, Gerstein & Borun LLP

(57) ABSTRACT

The disclosure relates to the detection of analytes (e.g., biological pathogens such as bacteria or viruses) using a conductive polymer label. The disclosed detection system utilizing the conductive polymer label generally involves the formation of an analyte conjugate between the target analyte and a conductive polymer moiety conjugated to the target analyte. The conductive polymer portion of the analyte conjugate is electrically activated to form an electrically activated analyte conjugate having an increased electrical conductivity relative to the analyte conjugate as originally formed. The electrically activated analyte conjugate can then be detected by any suitable means, such as by conductimetric or electrochemical detection.

17 Claims, 4 Drawing Sheets

(56) References Cited

U.S. PATENT DOCUMENTS

| | | | |
|---|---|---|---|
| 4,965,187 | A | 10/1990 | Tonelli |
| 5,166,078 | A | 11/1992 | McMahon et al. |
| 5,169,789 | A | 12/1992 | Bernstein |
| 5,177,014 | A | 1/1993 | O'Connor et al. |
| 5,219,725 | A | 6/1993 | O'Connor et al. |
| 5,256,372 | A | 10/1993 | Brooks et al. |
| 5,312,762 | A | 5/1994 | Guiseppi-Elie |
| 5,356,785 | A | 10/1994 | McMahon et al. |
| 5,491,097 | A | 2/1996 | Ribi et al. |
| 5,518,892 | A | 5/1996 | Naqui et al. |
| 5,536,644 | A | 7/1996 | Ullman et al. |
| 5,559,041 | A | 9/1996 | Kang et al. |
| 5,620,845 | A | 4/1997 | Gould et al. |
| 5,620,895 | A | 4/1997 | Naqui et al. |
| 5,627,026 | A | 5/1997 | O'Connor et al. |
| 5,656,448 | A | 8/1997 | Kang et al. |
| 5,670,031 | A | 9/1997 | Hintsche et al. |
| 5,695,928 | A | 12/1997 | Stewart |
| 5,700,655 | A | 12/1997 | Croteau et al. |
| 5,726,010 | A | 3/1998 | Clark |
| 5,726,013 | A | 3/1998 | Clark |
| 5,728,587 | A | 3/1998 | Kang et al. |
| 5,750,333 | A | 5/1998 | Clark |
| 5,753,456 | A | 5/1998 | Naqui et al. |
| 5,976,896 | A | 11/1999 | Kumar et al. |
| 5,985,594 | A | 11/1999 | Croteau et al. |
| 6,136,554 | A | 10/2000 | Bochner |
| 6,315,926 | B1 | 11/2001 | Jansen |
| 6,322,901 | B1 * | 11/2001 | Bawendi ............... C01B 17/20 257/E33.004 |
| 6,331,356 | B1 | 12/2001 | Angelopoulos et al. |
| 6,333,145 | B1 | 12/2001 | Cloots et al. |
| 6,333,425 | B1 | 12/2001 | Michot et al. |
| 6,478,938 | B1 | 11/2002 | Paek et al. |
| 7,541,004 | B2 | 6/2009 | Niksa et al. |
| 8,287,810 | B2 | 10/2012 | Alocilja et al. |
| 2003/0153094 | A1 | 8/2003 | Alocilja et al. |
| 2003/0170613 | A1 | 9/2003 | Straus |
| 2003/0178309 | A1 | 9/2003 | Huang et al. |
| 2005/0009002 | A1 | 1/2005 | Chen et al. |
| 2007/0020700 | A1 | 1/2007 | Carpenter et al. |
| 2008/0305963 | A1 | 12/2008 | Alocilja et al. |
| 2008/0314766 | A1 | 12/2008 | Alocilja et al. |
| 2009/0123939 | A1 | 5/2009 | Alocilja et al. |
| 2012/0295368 | A1 * | 11/2012 | Im ............... B82Y 5/00 436/501 |
| 2012/0322064 | A1 | 12/2012 | Alocilja et al. |

OTHER PUBLICATIONS

Park, J. et al., "Compact and stable quantum dots with positive, negative, or zwitterionic surface: specific cell interactions and non-specific adsorptions by the surface charges", Advanced Functional Materials (2011) 21:1558-1566.*

Chumbimuni-Torres, et al. Solid Contact Potentiometric Sensors for Trace Level Measurements, Anal. Chem. (Feb. 15, 2006); 78(4): 1318-1322.

Dubus et al., PCR-Free DNA Detection Using a Magnetic Bead-Supported Polymeric Transducer and Microelectromagnetic traps, Anal. Chem., 78(13):4457-64 (Jul. 1, 2006).

Farace et al., Reagentless Biosensing Using Electrochemical Impedance Spectroscopy. Bioelectrochemistry (Jan. 2002): 55(1-2):1-3.

Kim et al., Conductimetric Membrane Strip Immunosensor with Polyaniline-Bound Gold Colloids as Signal Generator. Bio and Bioelectronics (Feb. 2000); 14(12): 907-915.

Luo et al., s-Electron Ferromagnetism in Gold and Silver Nanoclusters. Nano Letters (Oct. 2007); 7(1): 3134-3137.

Muhammad-Tahir et al., (2003b), Fabrication of a Disposable Biosensor for *Escherichia coli* 0157:H7 Detection. IEEE Sensor Journal, 3(4), 345-351.

Pal et al., Nanowire Labeled Direct-Charge Transfer Biosensor for Detecting *Bacillus* Species, Biosens Bioelectron, vol. 22, pp. 2329-2936, 2007.

Park, et al., Array-Based Electrical Detection of DNA with Nanoparticle Probes. Sci. (Feb. 2002); 295(5559): 1503-1506.

Poddar et al., Magnetic Properties of Conducting Polymer Doped with Manganese—Zinc Ferrite Nanoparticles. Nanotechnology (Oct. 2004); 15(10): S570-S574.

Rosi, et al., Nanostructures in Biodiagnostics. Chem. Reviews (Apr. 2005); 105(4): 1547-1562.

Setterington et al., Immunomagnetic Extraction and Magnet-Aided Electrochemical Detection of Polyaniline-Labeled Cells, Biosensors 2010 presentation (May 26, 2010).

Setterington et al., Magnetic/Polyaniline Core/Shell Nanoparticles for Target Extraction and Electrical Detection of -Agents, Nano-DDS 2009 presentation (Sep. 29, 2009).

Setterington et al., Rapid Electrochemical Detection of Polyaniline-labeled *Escherichia coli* 0157:H7, (2011) 26, 2208-2214 (available online Sep. 25, 2010).

Sharma et al., Composition Dependent Magnetic Properties of Iron Oxide-Polyaniline Nanoclusters, Journal of Applied Physics 97, 014311(2005).

Stejskal J., Polyaniline. Preparation of a Conducting Polymer, Pure Appin. Chem., vol. 74, No. 5, pp. 857-867 (2002).

Zhu et al., Electrochemically Fabricated Polyaniline Nanowire-Modified Electrode for Voltammetric Detection of DNA Hybridization. Electro. Acta, 51, (2006) 3758-3762.

* cited by examiner

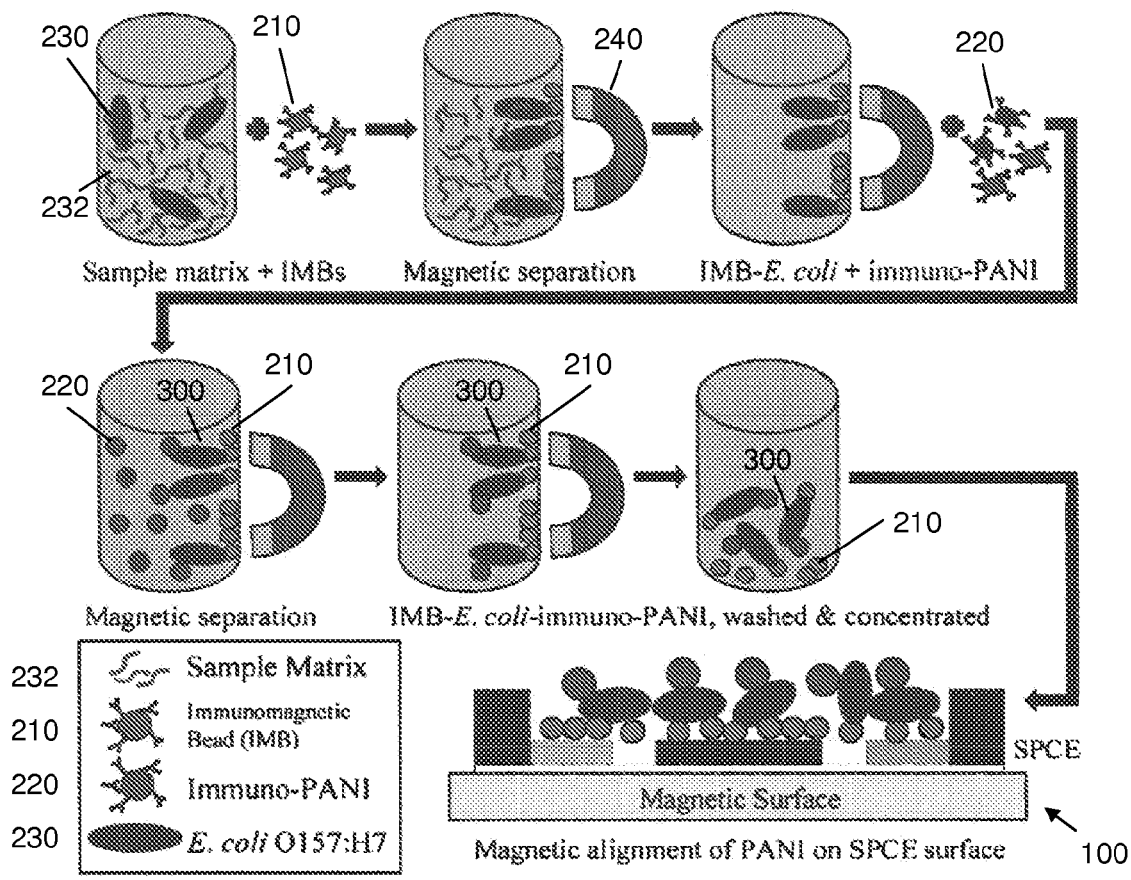
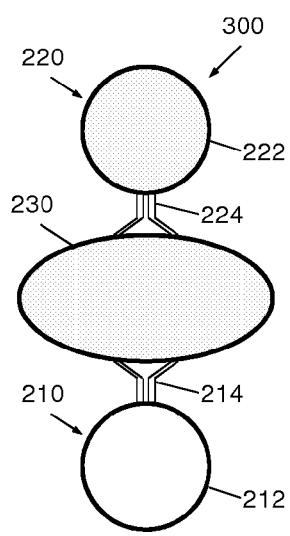 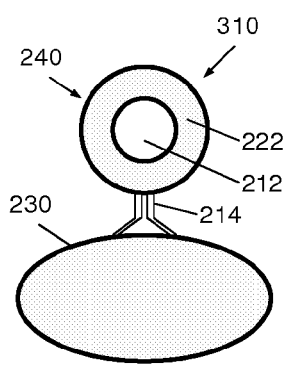 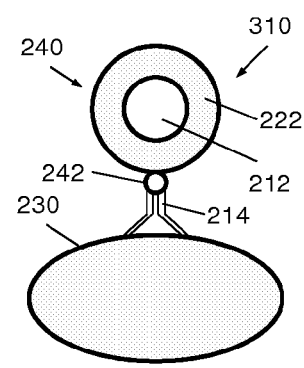
Figure 1A
Figure 1B    Figure 1C    Figure 1D

DETECTION OF CONDUCTIVE POLYMER-LABELED ANALYTES

CROSS-REFERENCE TO RELATED APPLICATION

This application is a division of U.S. patent application Ser. No. 13/477,205, filed May 22, 2012, which claims the priority benefit of U.S. Provisional Application No. 61/519,442, filed May 23, 2011, the entire contents of which are incorporated herein by reference in their entireties.

STATEMENT OF GOVERNMENT INTEREST

This invention was made with government support under 2007-ST-061-000003 awarded by the U.S. Department of Homeland Security. The government has certain rights in the invention.

BACKGROUND OF THE DISCLOSURE

1. Field of the Disclosure

The disclosure relates to the detection of analytes (e.g., biological pathogens such as bacteria or viruses) using a conductive polymer label. In an embodiment, a two-particle detection system includes immunofunctionalized conductive polymer nanoparticles as labels and immunofunctionalized magnetic nanoparticles as separators/concentrators for a particular target analyte.

2. Brief Description of Related Technology

Bacterial infections are a major source of human disease and fatalities. Dangerous bacterial pathogens may be present in nearly any environment and are imperceptible to the human senses. *Escherichia coli* O157:H7, for example, is a common food- and water-borne pathogen which can cause illness and death with a dose as low as 10 cells. *Bacillus anthracis*, the causative agent of the severe and fatal disease anthrax, is a likely organism for use in bioterrorism due to its low infectious dose and ability to withstand harsh conditions. The traditional method of identifying such pathogens involves culturing unknown cells in a controlled laboratory setting until colonies are visibly detectable, which requires anywhere from 24 hours to several months, depending on the species.

Alocilja et al. U.S. Publication Nos. 2003/0153094, 2008/0314766, 2009/0123939, generally relate to biosensor devices and/or BEAM nanoparticle compositions and are incorporated herein by reference in their entireties.

SUMMARY

The disclosed detection platform employs immunomagnetic separation and electrochemical detection of various pathogens, including viral or bacterial pathogens such as *E. coli* O157:H7, and detection is based on a conductive polymer label such as polyaniline. In an embodiment, the polyaniline-labeled *E. coli* O157:H7 cells are readily detected by cyclic voltammetry on disposable screenprinted carbon electrode (SPCE) sensors. An external magnetic field is employed to pull the labeled cells to the electrode surface, in order to amplify the electrochemical signal generated by the polyaniline. A representative biosensor assay requires only 70 min and can detect the presence of as few as 7 CFU of *E. coli* O157:H7 on the SPCE.

In one aspect, the disclosure provides a method for detecting the presence of a target analyte (e.g., a bacterium or virus of a particular genus, species, or strain), the method comprising: (a) providing an analyte conjugate comprising: (i) the target analyte and (ii) a conductive polymer moiety conjugated to the target analyte; (b) electrically activating the analyte conjugate, thereby forming an electrically activated analyte conjugate having an increased electrical conductivity relative to the analyte conjugate; and (c) detecting the electrically activated analyte conjugate (e.g., to further determine that the target analyte is present in a sample from which the analyte conjugate is formed). In an embodiment, detecting the electrically activated analyte conjugate in part (c) comprises conductimetrically or electrochemically detecting the conductive polymer moiety of the electrically activated analyte conjugate. In another embodiment, detecting the electrically activated analyte conjugate in part (c) comprises performing cyclic voltammetry to detect the conductive polymer moiety of the electrically activated analyte conjugate. Electrical activation of the analyte conjugate in part (b) can comprise acid-doping the analyte conjugate. In an embodiment, the analyte conjugate is provided in part (a) in a liquid aqueous medium having a pH value of 5 or more, and the analyte conjugate is electrically activated in the liquid aqueous medium in part (b). In another embodiment, the method further comprises, before detecting the electrically activated analyte conjugate in part (c), immobilizing the analyte conjugate or the electrically activated analyte conjugate on a detection surface of a biosensor (e.g., immobilizing the analyte conjugate on the detection surface before electrically activating the analyte conjugate in part (b); immobilizing the already-formed electrically activated analyte conjugate on the detection surface).

In another aspect, the disclosure relates to a system for binding a target analyte, the system comprising: (a) a magnetic nanoparticle capture composition comprising: (i) a magnetic nanoparticle; and (ii) a first binding pair member bound to the magnetic nanoparticle, the first binding pair member being capable of specifically binding to the target analyte; (b) a conductive polymer nanoparticle label composition comprising: (i) a conductive polymer nanoparticle, and (ii) a second binding pair member bound to the conductive polymer nanoparticle, the second binding pair member being capable of specifically binding to the target analyte; optionally (c) a biosensor comprising a detection surface having opposing top and bottom surfaces (e.g., when the top surface is configured/adapted to receive a sample to be analyzed); and optionally (d) a magnetic means for generating a magnetic field positioned adjacent the bottom surface of the detection surface.

In another aspect, the disclosure relates to a target analyte triplex comprising: (a) a magnetic nanoparticle capture composition comprising: (i) a magnetic nanoparticle; and (ii) a first binding pair member bound to the magnetic nanoparticle, the first binding pair member being capable of specifically binding to the target analyte; (b) a conductive polymer nanoparticle label composition comprising: (i) a conductive polymer nanoparticle, and (ii) a second binding pair member bound to the conductive polymer nanoparticle, the second binding pair member being capable of specifically binding to the target analyte; and (c) the target analyte bound to both the first binding pair member and the second binding pair member.

In another aspect, the disclosure relates to a biologically enhanced, electrically active magnetic (BEAM) nanoparticle composition for specifically binding a target analyte, the composition comprising: (a) a particulate composition comprising a conductive polymer bound to magnetic nanoparticles; and, (b) an immunoconjugate binding pair member bound to the conductive polymer of the particulate composition, the immunoconjugate comprising: (i) an immunoglobulin comprising (A) an Fc region and (B) an antigen-binding region being capable of specifically binding to the target analyte, and (ii) an immunoglobulin-binding protein having a binding affinity to the Fc region of the immunoglobulin, the immunoglobulin-binding protein being bound to the conductive polymer and the Fc region of the immunoglobulin. Suitably, the immunoconjugate is oriented so that the antigen-binding region of the immunoglobulin is outwardly directed relative to the conductive polymer and the magnetic nanoparticle of the particulate composition (e.g., each core/shell nanoparticle has a plurality of immunoconjugates preferentially oriented such that the antigen-binding regions are generally outwardly pointing in the aggregate). In an embodiment, the immunoglobulin-binding protein comprises a bacterial surface protein (e.g., recombinant form thereof, a derivative thereof, and/or a recombinant fusion protein thereof), for example an immunoglobulin-binding protein selected from the group consisting of protein A, protein G, protein A/G, and combinations thereof. In an embodiment, the immunoglobulin is selected from the group consisting of IgA, IgD, IgE, IgG, IgM, subclasses thereof, and combinations thereof.

Various refinements of the disclosed methods, systems, apparatus, and compositions are possible. For example, the analyte conjugate can comprise: (i) a magnetic nanoparticle capture composition comprising: (A) a magnetic nanoparticle, and (B) a first binding pair member bound to the magnetic nanoparticle, the first binding pair member being capable of specifically binding to the target analyte, (ii) a conductive polymer nanoparticle label composition comprising: (A) a conductive polymer nanoparticle, and (B) a second binding pair member bound to the conductive polymer nanoparticle, the second binding pair member being capable of specifically binding to the target analyte, and (iii) the target analyte bound to both the first binding pair member and the second binding pair member. In another refinement, the analyte conjugate comprises: (i) a particulate composition comprising a conductive polymer as the conductive polymer moiety bound to a magnetic nanoparticle, (ii) a binding pair member bound to the conductive polymer of the particulate composition, the binding pair member being capable of specifically binding to the target analyte, and (iii) the target analyte bound to the binding pair member. Regardless of the particular type of particle system used for forming the analyte conjugate, (i) the magnetic nanoparticles can comprise at least one of Fe(II) and Fe(III); and (ii) the conductive polymer (e.g., as a nanoparticle itself or as a shell to the magnetic nanoparticle) can be selected from the group consisting of polyanilines, polypyrroles, polythiophenes, derivatives thereof, combinations thereof, blends thereof with other polymers, and copolymers of the monomers thereof. In another refinement, the biosensor is a screen-printed carbon electrode (SPCE), and the detection surface is a working electrode of the SPCE.

In another refinement, a magnet can be used to immobilize and amplify the signal of a conductive polymer label in a biosensor. For example, in an embodiment, (i) the detection surface of the biosensor has opposing top and bottom surfaces, where the electrically activated analyte conjugate is immobilized on the top surface; (ii) the biosensor further comprises a magnetic means for generating a magnetic field positioned adjacent the bottom surface of the detection surface; (iii) the electrically activated analyte conjugate further comprises a magnetic moiety conjugated to the target analyte or bound to the conductive polymer of the electrically activated analyte conjugate; and (iv) immobilizing the analyte conjugate or the electrically activated analyte conjugate comprises (A) generating the magnetic field with the magnetic means to magnetically position the analyte conjugate or the electrically activated analyte conjugate closer to the top surface of the detection surface than in the absence of the magnetic field, and (B) maintaining the magnetic field when detecting the electrically activated analyte conjugate in part (c) (e.g., on an electrode detection surface such as the working electrode of an SPCE). In a further refinement, (i) the biosensor comprises a binding pair member capable of specific or non-specific binding to the target analyte, the binding pair member being immobilized on the detection surface; and (ii) immobilizing the analyte conjugate or the electrically activated analyte conjugate comprises (A) first immobilizing the analyte conjugate or the electrically activated analyte conjugate on the detection surface through a binding interaction between the binding pair member and the target analyte of the analyte conjugate or the electrically activated analyte conjugate, (B) washing the detection surface in the absence of a magnetic field, (C) generating the magnetic field with the magnetic means to magnetically position the analyte conjugate or the electrically activated analyte conjugate closer to the top surface of the detection surface than in the absence of the magnetic field, and (D) maintaining the magnetic field when detecting the electrically activated analyte conjugate in part (c).

The present disclosure also relates to a method for detecting the presence of a microorganism in an aqueous solution in a magnetically transparent container, the method comprising: (a) collecting a first conjugate on the container comprising: (i) the microorganism; and (ii) a conductive polymer moiety conjugated between the microorganism and first magnetic nanoparticles using a magnet outside the container; (b) collecting a second conjugate comprising an immunogen-conductive polymer conjugate with second magnetic nanoparticles, thereby forming an electrically activated microorganism conjugate with the first and second conjugates with the first and second magnetic nanoparticles; and (c) detecting the microorganism. Further, the present disclosure relates to a polyaniline conductive polymer as the conductive polymer moiety bound to the first and second magnetic nanoparticles. Still further, the present disclosure relates to an (i) immunoglobulin comprising (A) an Fc region and (B) an antigen-binding region being capable of specific binding to the microorganism, and (ii) an immunoglobulin-binding protein having a binding affinity to the Fc region of the immunoglobulin, the immunoglobulin-binding protein being bound to the conductive polymer and the Fc region of the immunoglobulin. Further, the present disclosure relates to a the solution of the conjugate in step (b) comprises a strong acid to enhance electrical activation (e.g., contacting with a strong acid such as HCl, $HNO_3$, $H_2SO_4$, or a weak acid). Still further, the present disclosure relates to the microorganism which is provided in part (a) in the liquid aqueous solution which has a pH value of 5 or more (e.g., more generally liquid media having non-acidic, approximately neutral, or a physiological pH value; such as >5, >6, >7, 6-9, 7-8; the liquid aqueous solution can comprise pH buffer components and can be the medium in which a sample containing the microorganism is incubated to form the analyte conjugate with the conductive polymer moiety). Still further, the present disclosure relates to the detecting of the microorganism in part (c) comprises conductimetrically or electrochemically detecting the electrically activated microorganism in step (a). Further, the present disclosure relates to detecting the electrically activated microorganism is immobilized on a working electrode and adjacent a counter/reference electrode of an electrochemical biosensor device for conductimetric or electrochemical detection. Furthermore, the present disclosure relates to detecting the electrically activated microorganism is immobilized on a detection surface and between opposing electrodes of an electrochemical biosensor device for performing conductimetric or electrochemical detection. Further, the present disclosure relates to detecting the electrically activated microorganism in part (c) which comprises performing cyclic voltammetry to detect the conductive polymer moiety of the electrically activated microorganism. Still further, the present disclosure relates to detecting the electrically activated microorganism in part (c), immobilizing the microorganism or the electrically activated microorganism on a detection surface of a biosensor. Further, the present disclosure relates to immobilizing the microorganism on the detection surface before electrically activating the microorganism in part (b). Further, the present disclosure relates to immobilizing the electrically activated microorganism on the detection surface. Still further, the present disclosure relates to (i) the biosensor comprises a binding pair member specific to the microorganism, the binding pair member being immobilized on the detection surface, and (ii) the microorganism of the electrically activated microorganism is bound to the microorganism when detecting the electrically activated microorganism in part (c). Furthermore, the present disclosure relates to (i) the biosensor comprises a non-specific binding pair member of non-specific binding to the microorganism, the non-specific binding pair member being immobilized on the detection surface, and (ii) the microorganism of the electrically activated microorganism is bound to the non-specific binding pair member when detecting the electrically activated microorganism in part (c). Furthermore, the present disclosure relates to (i) the detection surface of the biosensor has opposing top and bottom surfaces, where the electrically activated microorganism is immobilized on the top surface; (ii) the biosensor further comprises a magnetic means for generating a magnetic field positioned adjacent the bottom surface of the detection surface; and (iii) immobilizing the microorganism or the electrically activated microorganism by (A) generating the magnetic field with the magnetic means to magnetically position the microorganism or the electrically activated microorganism closer to the top surface of the detection surface than in the absence of the magnetic field, and (B) maintaining the magnetic field when detecting the electrically activated microorganism in part (c) (e.g., on an electrode detection surface such as the working electrode of an SPCE). Still further, the present disclosure relates to (i) the biosensor comprises a microorganism capable of binding to the microorganism, the microorganism being immobilized on the detection surface; (ii) immobilizing the microorganism or the electrically activated microorganism which comprises (A) first immobilizing the microorganism or the electrically activated microorganism on the detection surface through a binding interaction between the binding pair member and the microorganism of the microorganism or the electrically activated microorganism, (B) washing the detection surface in the absence of a magnetic field, (C) generating the magnetic field with the magnetic means to magnetically position the microorganism or the electrically activated microorganism closer to the top surface of the detection surface than in the absence of the magnetic field, and (D) maintaining the magnetic field when detecting the electrically activated microorganism in part (c).

Also, the present disclosure relates to the biosensor is a screen-printed carbon electrode (SPCE), and the detection surface is a working electrode of the SPCE. Still further, the present disclosure relates to the genus or species of the microorganism present in a sample. Furthermore, the present disclosure relates to the conductive polymer moiety which is selected from the group consisting of polyanilines, polypyrroles, polythiophenes, derivatives thereof, combinations thereof, blends thereof with other polymers, and copolymers of the monomers thereof. Still further, the present disclosure relates to the microorganism which is selected from the group consisting of a bacterium and a virus. Furthermore, the present disclosure relates to a system for binding a microorganism, the system comprising: (a) reagents to perform the method.

Finally, the present disclosure relates to a biologically enhanced, electrically active magnetic (BEAM) nanoparticle composition for binding a microorganism, the composition comprising: (a) a particulate composition comprising a conductive polymer bound to magnetic nanoparticles; and, (b) an immunoconjugate binding pair member bound to the conductive polymer of the particulate composition, the immunoconjugate comprising: (i) an immunoglobulin comprising immune-conductive polymer conjugate (A) an Fc region and (B) an antigen-binding region being capable of binding to the microorganism, and (ii) an immunoglobulin-binding protein having a binding affinity to the Fc region of the immunoglobulin, the immunoglobulin-binding protein being bound to the conductive polymer and the Fc region of the immunoglobulin. Furthermore, the present disclosure relates to the BEAM nanoparticle composition, wherein the immunoconjugate is oriented so that the antigen-binding region of the immunoglobulin is outwardly directed relative to the conductive polymer and the magnetic nanoparticle of the particulate composition (e.g., each core/shell nanoparticle has a plurality of immunoconjugates preferentially oriented such that the antigen-binding regions are generally outwardly pointing in the aggregate). Still further, the present disclosure relates to the BEAM nanoparticle composition, wherein the immunoglobulin-binding protein comprises a bacterial surface protein (e.g., recombinant form thereof, a derivative thereof, and/or a recombinant fusion protein thereof). Further still, the present disclosure relates to the BEAM nanoparticle composition, wherein the immunoglobulin-binding protein is selected from the group consisting of protein A, protein G, protein A/G, and combinations thereof. Furthermore, the present disclosure relates to the BEAM nanoparticle composition, wherein the immunoglobulin is selected from the group consisting of IgA, IgD, IgE, IgG, IgM, subclasses thereof, and combinations thereof. Further, the present disclosure relates to the BEAM nanoparticle composition, wherein: (i) the immunoglobulin-binding protein comprises protein A; and (ii) the immunoglobulin comprises IgG. Further still, the present disclosure relates to the BEAM nanoparticle composition, wherein: (i) the magnetic nanoparticles comprise at least one of Fe(II) and Fe(III); and, (ii) the conductive polymer is selected from the group consisting of polyanilines, polypyrroles, polythiophenes, derivatives thereof, combinations thereof, blends thereof with other polymers, and copolymers of the monomers thereof. Also, the present disclosure relates to the BEAM nanoparticle composition, wherein the microorganism is selected from the group consisting of a bacterium and a virus. Lastly, the present disclosure relates to the BEAM nanoparticle composition, further comprising: (c) the microorganism bound to the antigen-binding region of the immunoglobulin in the immunoconjugate.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples, drawings, and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein:

FIG. 1A illustrates compositions, apparatus, and method steps for detecting an analyte with a conductive polymer label.

FIGS. 1B-1D illustrate various analyte conjugates according to the disclosure and incorporating a conductive polymer label.

Figure 1E:
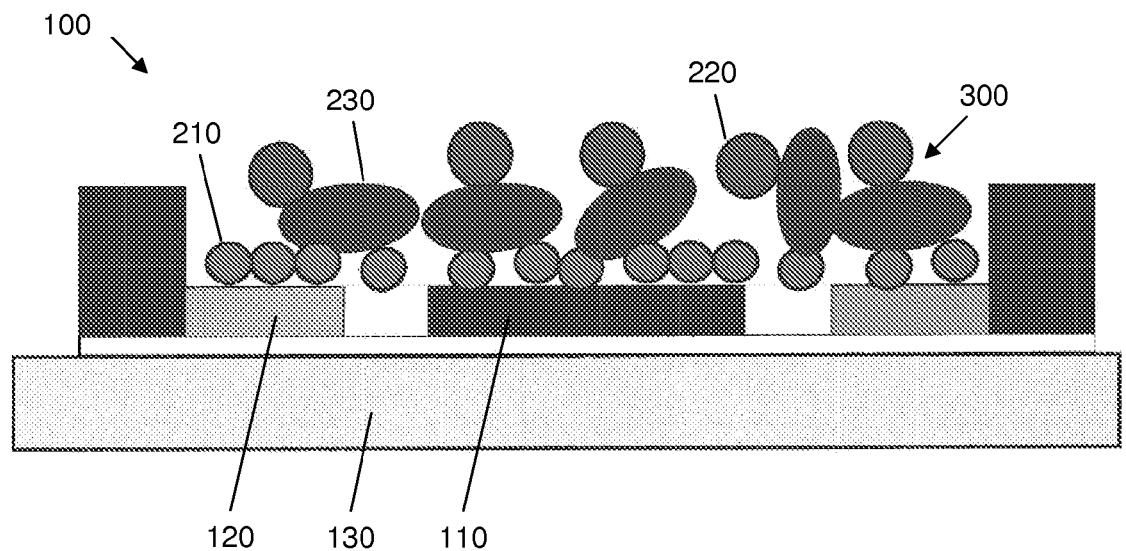
FIGS. 1E and 1F illustrate a side view (1E) and a top view (1F) of a biosensor for detecting an analyte conjugate with a conductive polymer label.

While the disclosed compositions, kits, apparatus, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure relates to the detection of analytes (e.g., biological pathogens such as bacteria or viruses) using a conductive polymer label. In a specific example described herein, a two-particle detection system includes immuno-functionalized conductive polymer nanoparticles as labels and immunofunctionalized magnetic nanoparticles as separators/concentrators, each being capable of specifically binding to a desired target analyte. Representative nanoparticles can be synthesized from gamma iron-oxide templates and electrically-active polymers such as polyaniline.

The disclosed detection system utilizing the conductive polymer label generally involves the formation of an analyte conjugate between the target analyte and a conductive polymer moiety conjugated to the target analyte. The conductive polymer portion of the analyte conjugate is electrically activated to form an electrically activated analyte conjugate having an increased electrical conductivity relative to the analyte conjugate as originally formed (e.g., by contacting the conductive polymer label with the target analyte in an aqueous sample medium). The electrically activated analyte conjugate (e.g., the electrically re-activated conductive polymer label thereof) can then be detected by any suitable means, such as by conductimetric or electrochemical detection (e.g., cyclic voltammetry to detect the conductive polymer moiety of the electrically activated analyte conjugate).

FIGS. 1A-1F show schematic representations of various elements of a detection system utilizing a conductive polymer label according to the disclosure. In one embodiment, the detection principle involves an electrochemical sandwich assay engaging a magnetic nanoparticle capture probe 210 and a conductive polymer nanoparticle probe/label 220. The magnetic capture probe 210 includes a first binding pair member 214 (e.g., specific binding pair member such as antibody or oligonucleotide) conjugated with a magnetic nanoparticle 212, whereas the conductive polymer label 220 includes a second binding pair member 224 (e.g., specific binding pair member such as antibody or oligonucleotide, which can be the same as or different from the first binding pair member 214) conjugated with a conductive polymer nanoparticle 222. The capture probe 210 and the conductive polymer label 220 are combined with a target analyte 230 (e.g., in a sample medium 232 to be tested or other liquid medium), where the target analyte 230 undergoes sandwiched binding with both probes 210, 220 (e.g., specific or non-specific binding depending on the type of binding pair members 214, 224 used) to form an analyte conjugate 300. As illustrated in FIG. 1A, the probes 210, 220 may be added sequentially to the sample 232, for example to first form a probe 210-target 230 conjugate that can be magnetically separated (e.g., with a magnet 240) and washed/concentrated from other sample 232 components (e.g., non-target interfering components) prior to the addition of the label 220 to form the analyte conjugate 300.

In the case illustrated in FIG. 1A, the capture probe 210 and the conductive polymer label 220 have respective antibodies 214, 224 as specific binding pair members that specifically bind to regions of the target analyte 230 (e.g., different portions/active sites of a bacterium), thus forming a triplex 300 between the capture probe 210, the target analyte 230, and the label 220 as the analyte conjugate 300 (FIG. 1B). The conjugates 300 thus formed are separated from other non-target sample components and unreacted target analytes 230 by magnetic separation of the unbound capture probe 210 nanoparticles and the bound capture probe 210 nanoparticles in the analyte conjugate 300 (e.g., by magnetic immobilization of the nanoparticles 210, 300 combined with washing of the non-immobilized sample medium and sample components). Subsequently, the analyte conjugates 300 are added to the surface of a biosensor 100 (e.g., illustrated as a working electrode 110 of a screen-printed carbon electrode (SPCE) biosensor 100). The target analytes 230 can be detected on the biosensor 100 surface through the redox properties of the conductive polymer label 220, for example using cyclic voltammetry to detect the presence of the conjugates/triplexes 300 based on the conductive properties of the conductive polymer therein.

Prior to detecting the analyte conjugate 300, the conductive polymer component 222 thereof is suitably electrically activated. Conductive polymers are suitably acid-doped/electrically activated when initially formed. However, samples 232 to be analyzed for the presence of the target analyte 230 can be buffered or otherwise at a generally neutral pH when the conjugate 300 is formed. For example, the analyte conjugate 300 is generally formed in a liquid aqueous medium having a pH value of 5 or more (e.g., more generally a sample medium being non-acidic, approximately neutral, or having a physiological pH value; for example a medium with a pH value at least 5, 6, or 7, and/or up to 8 or 9, such as a liquid aqueous sample medium including pH buffer components in which a sample containing the target analyte is incubated to form the analyte conjugate with the conductive polymer moiety). In such an environment, the conductive polymer component 222 of the conjugate 300 may become relatively electrically de-activated (e.g., having an electrical conductivity less than when originally formed/synthesized). Electrical re-activation forms an electrically activated analyte conjugate 300 having an increased electrical conductivity relative to the conjugate 300 as originally formed (e.g., where the electrical conductivity of the conductive polymer as originally formed from a sample can be reduced during sample capture, extraction, and concentration steps). Suitable methods for re-activation include acid-doping the analyte conjugate 300, such as by contacting it with a strong acid (e.g., a mineral acid such as HCl, $HNO_3$, $H_2SO_4$) or a weak acid. Electrical re-activation can be performed before application of the conjugate 300 to the biosensor 100 (e.g., in the liquid medium where the conjugate 300 was formed) or after application of the conjugate 300 to the biosensor 100.

FIGS. 1C and 1D illustrate alternate embodiments for an analyte conjugate 310 including a conductive polymer label. As illustrated, a nanoparticulate combined capture probe/label 240 includes a conductive polymer shell 222 as the conductive polymer label moiety bound to a magnetic nanoparticle core 212. The capture probe/label 240 includes a first binding pair member 214 (e.g., specific binding pair member such as antibody or oligonucleotide) conjugated with the conductive polymer shell 222 for forming the analyte conjugate 310 with the target analyte 230. As shown in FIG. 1D, an immunoglobulin-binding protein 242 (e.g., protein A) can be used to immobilize the first binding pair member 214 in the form of an immunoglobulin with a preferable, outwardly directed orientation for the immunoglobulin's active sites.

The analyte conjugate 300, 310 may be immobilized on the biosensor 100 surface 110 prior to detection. For example, the conjugate 300, 310 may be immobilized on a detection surface and between opposing electrodes of an electrochemical biosensor device or immobilized on a working electrode and adjacent a counter/reference electrode of an electrochemical biosensor. In some embodiments, the immobilization surface may be modified/functionalized with a specific or non-specific binding pair member for anchoring the conjugate 300, 310 thereto by specific or non-specific binding interactions (e.g., with the target analyte 230 or other component of the conjugate 300, 310). After a short incubation period, the biosensor 100 surface is washed to remove excess capture probes 210 (e.g., which have no conductive polymer label 220 and/or target analyte 230 bound thereto) and unbound conjugates 300, 310 (e.g., which may not have had sufficient contact with the biosensor surface for attachment/immobilization). In other embodiments, immobilization of the conjugate may be additionally or alternatively performed using a magnet 130 positioned below the immobilization surface 110 of the biosensor 100. Application of a magnetic field with the magnet 130 immobilizes the conjugate 300, 310 and pulls it tightly against the immobilization surface 110 to enhance a subsequent conductimetric or electrochemical measurement. In this case, capture probes 210 that are unbound to other constituents may be retained on the biosensor 100; however, the absence of a corresponding conductive polymer label 220 in the conjugate 300, prevents the unbound capture probes 210 from contributing to a false positive result. In some embodiments, the biosensor is not functionalized with a specific or non-specific binding pair member/immobilization agent, for example where the magnet 130 is the only means for conjugate 300, 310 immobilization.

Figure 1F:
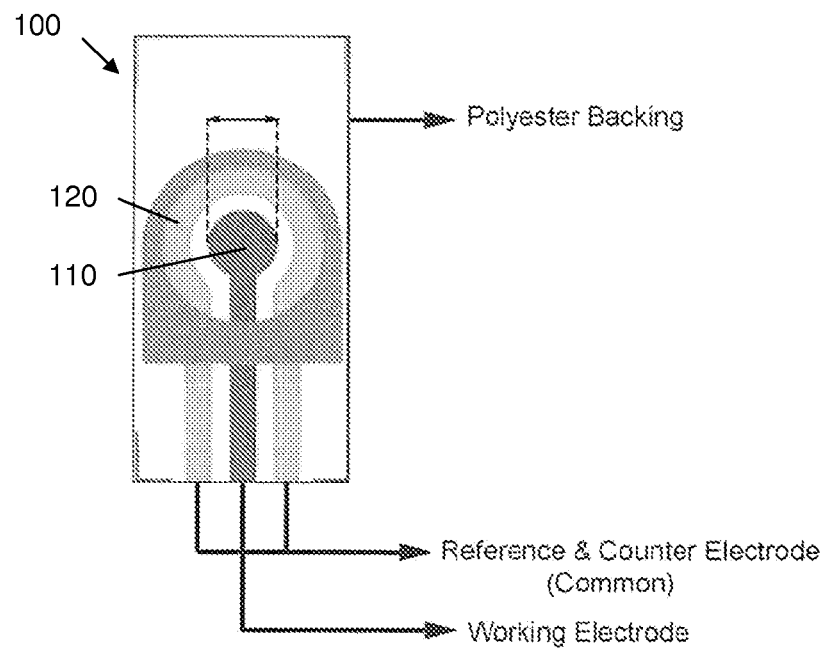

FIGS. 1E and 1F illustrate the structure of a screen-printed carbon electrode (SPCE) as a representative biosensor 100 having a reference/counter electrode 120 and a working electrode 110 onto which the analyte conjugate 300 (or 310) is applied or immobilized for detection. As illustrated, the magnet 130 is positioned below the biosensor 100 components 110, 120 such that application of a magnetic field with the magnet 130 enhances the ability of the biosensor to detect the conductive polymer portion of the conjugate 300, 310.

Magnetic and Conductive Polymer Particulate Compositions

Suitable nanoparticle compositions according to the disclosure are illustrated in FIGS. 1B-1D. A two-particle detection system includes a magnetic nanoparticle capture probe 210 and a conductive polymer nanoparticle probe/label 220. A single particle detection system includes a combined capture probe/label 240 including a conductive polymer bound to magnetic nanoparticles (e.g., a population of magnetic nanoparticles in which each nanoparticle generally has at least some conductive polymer bound thereto, such as a magnetic nanoparticle core with a conductive polymer shell). The probes/labels according to the disclosure include binding pair members for binding to the target analyte. U.S. Publication No. 2009/0123939, the entire contents of which are hereby incorporated herein by reference, discloses particulate compositions, biologically enhanced particulate compositions and related methods suitable for use according to the present disclosure.

The conductive properties of the conductive polymer (sometimes referenced as a synthetic metal) arise from the π-electron backbone and the single/double bonds of the π-conjugated system alternating down the polymer chain. Some conducting polymeric structures include polyaniline (PANi), polypyrrole, polyacetylene, and polyphenylene. Polyaniline, in particular, has been studied thoroughly because of its stability in fluid form, conductive properties, and strong bio-molecular interactions. Conductive polymers can be used in a biosensor, an analytical device capable of pathogen detection in which the conductive polymers act as electrochemical transducers to transform biological signals to electric signals that can be detected and quantified.

The conductive polymers according to the disclosure are not particularly limited and generally include any polymer that is electrically conductive. Preferably, the conductive polymer is fluid-mobile when bound to an analyte. Suitable examples of conductive polymers are polyanilines, polypyrrole, and polythiophenes, which are dispersible in water and are conductive because of the presence of an anion or cation in the polymer (e.g., resulting from acid-doping of the polymer or monomer). Other electrically conductive polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. Conductive polyanilines are preferred. Polyaniline is perhaps the most studied conducting polymer in a family that includes polypyrrole, polyacetylene, and polythiophene. As both electrical conductor and organic compound, polyaniline possesses flexibility, robustness, highly controllable chemical and electrical properties, simple synthesis, low cost, efficient electronic charge transfer, and environmental stability. Addition of a protic solvent such as hydrochloric acid yields a conducting form of polyaniline, with an increase in conductivity of up to ten orders of magnitude. Illustrative are the conductive polymers described in U.S. Pat. Nos. 6,333,425, 6,333,145, 6,331,356 and 6,315,926. Preferably, the conductive polymers do not contain metals in their metallic form.

The conductive polymer provides a substrate for the subsequent attachment of a binding pair member (e.g., an antibody or an oligonucleotide) bound thereto, which binding pair member is complementary to a target analyte and thereby forms a nanoparticle capture probe or label, as described below. The electrically conductive characteristics of the conductive polymer also can facilitate detection of an analyte bound to the conductive polymer nanoparticle, for example by measuring the electrical resistance or conductance through a plurality of conductive polymer nanoparticles immobilized in a capture region of conductimetric biosensor device.

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma$-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma$-$Fe_2O_3$ is Sigma-Aldrich (St. Louis, Mo.), which is available as a nano-powder having particles sized at <50 nm with a specific surface area ranging from about 50 $m^2$/g to about 250 $m^2$/g. Preferably, the magnetic nanoparticles have a small size distribution (e.g., ranging from about 5 nm to about 25 nm) and uniform surface properties (e.g., about 50 $m^2$/g to about 245 $m^2$/g.).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula M1 $Fe_2O_4$, wherein M1 represents a divalent ion selected from Mn, Co, Ni, Cu, Zn, or Ba, pure or in admixture with each other or in admixture with ferrous ions. Other metal oxides include aluminium oxide, chromium oxide, copper oxide, manganese oxide, lead oxide, tin oxide, titanium oxide, zinc oxide and zirconium oxide, and suitable metals include Fe, Cr, Ni or magnetic alloys.

The various particulate compositions can be generally formed by the polymerization of a conductive polymer monomer (e.g., aniline, pyrrole) in a solution (e.g., aqueous) either containing the magnetic nanoparticles (e.g., to form a combined core/shell magnetic nanoparticle with the conductive polymer) or without the magnetic nanoparticles (e.g., to form a nanoparticle from the conductive polymer alone). The polymerization solution generally includes an acid dopant (e.g., HCl) to impart electrical conductivity to the resulting polymer. The polymerization reaction is preferably initiated by the addition of an oxidant (e.g., ammonium persulfate). Upon completion of the polymerization reaction, the solution contains the particulate composition in which the resulting conductive polymer is bound to the magnetic nanoparticles or in the form of nanoparticles itself. The magnetic nanoparticles and the conductive polymer monomer can be combined in any suitable weight ratio in the polymerization solution so that the resulting particulate composition has a desired balance of magnetic, electrical, and particle size properties. For example, the weight ratio of monomer:magnetic nanoparticles in the polymerization solution (or conductive polymer:magnetic nanoparticles in the resulting particulate composition) preferably ranges from about 0.01 to about 10, more preferably from about 0.1 to about 1 or about 0.4 to about 0.8, for example about 0.6. Similarly, the particulate composition preferably ranges in size (e.g., average size or size distribution range) from about 1 nm to about 500 nm, more preferably about 10 nm to about 200 nm, or about 50 nm or 80 nm to about 100 nm or 120 nm, for example at least about 1 nm, 10 nm, 20 nm, or 50 nm and/or up to about 50 nm, 80 nm, 100 nm, 120 nm, or 200 nm (e.g., for either the conductive polymer nanoparticle or the combined magnetic nanoparticle with conductive polymer shell).

Biologically Enhanced Nanoparticles

The particulate composition in any of its above embodiments can be extended to a biologically enhanced, nanoparticle composition by further including a binding pair member (e.g., specific binding pair member) bound to the conductive polymer of the particulate composition. The binding pair member is selected to be complementary to a target analyte so that the biologically enhanced nanoparticle composition can be used for the selective detection of the target analyte in a sample.

An analyte (or target analyte) generally includes a chemical or biological material, including living cells, in a sample which is to be detected using the biologically enhanced nanoparticle composition or other analyte probe. The analyte can include pathogens of interest (e.g., bacterial pathogens such as *E. coli* O157:H7, *B. anthracis, B. cereus*, in addition to those listed above). The analyte also may be an antigen, an antibody, a ligand (i.e., an organic compound for which a receptor naturally exists or can be prepared, for example one that is mono- or polyepitopic, antigenic, or haptenic), a single compound or plurality of compounds that share at least one common epitopic site, and a receptor (i.e., a compound capable of binding to an epitopic or determinant site of a ligand, for example thyroxine binding globulin, antibodies, enzymes, Fab fragments, lectins, nucleic acids, protein A, complement component C1q). In some embodiments, the term "analyte" also can include an analog of the analyte (i.e., a modified form of the analyte which can compete with the analyte for a receptor) that can also be detected using the biologically enhanced nanoparticle composition.

A sample generally includes an aliquot of any matter containing, or suspected of containing, the target analyte. For example, samples can include biological samples, such as samples from taken from animals (e.g., saliva, whole blood, serum, plasma, urine, tears, milk, and the like), cell cultures, plants; environmental samples (e.g., water); industrial samples; and food samples (e.g., solid or liquid foods in raw or processed form, such as milk). Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample. Accordingly, a sample to be tested by contact with an analyte probe can be a liquid medium containing the analyte, where the liquid medium can be the raw sample to be tested (e.g., milk), or it can be a liquid medium (e.g., a buffer) to which a solid or liquid raw sample to be tested is added.

The specific binding pair member generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, and whole cells are not immunological pairs, but can be used as binding pair members within the context of the present disclosure.

Preferably, the binding pair members are specific to each other and are selected such that one binding pair member is the target analyte of interest or a component thereof (e.g., a specific surface protein or other surface component of specific bacteria or other pathogen of interest), and the other binding pair member is the constituent bound to the conductive polymer of the particulate composition. Binding specificity (or specific binding) refers to the substantial recognition of a first molecule for a second molecule (i.e., the first and second members of the binding pair), for example a polypeptide and a polyclonal or monoclonal antibody, an antibody fragment (e.g., a Fv, single chain Fv, Fab', or F(ab')$_2$ fragment) specific for the polypeptide, enzyme-substrate interactions, and polynucleotide hybridization interactions. Preferably, the binding pair members exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules).

Substantial binding specificity refers to an amount of specific binding or recognition between molecules in an assay mixture under particular assay conditions. Substantial binding specificity relates to the extent that the first and second members of the binding pair to bind only with each other and do not bind to other interfering molecules that may be present in the analytical sample. The specificity of the first and second binding pair members for each other as compared to potential interfering molecules should be sufficient to allow a meaningful assay to be conducted for the target analyte. The substantial binding specificity can be a function of a particular set of assay conditions, which includes the relative concentrations of the molecules, the time and temperature of an incubation, etc. For example, the reactivity of one binding pair member with an interfering molecule as compared to that with the second binding pair member is preferably less than about 25%, more preferably less than about 10% or about 5%.

A preferred binding pair member is an antibody (an immunoglobulin) that specifically binds to and is thereby defined as complementary with a particular spatial and polar organization of another molecule (e.g., an antigen). Antibodies generally include Y-shaped proteins on the surface of B cells that specifically bind to antigens such as bacteria, viruses, etc. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained.

The specific binding pair member that is specific to the target analyte can be bound directly or indirectly to the conductive polymer of the particulate composition (or to the detection moiety of the analyte probe more generally) by any of a variety of methods known in the art appropriate for the particular binding pair member (e.g., antibody, DNA oligonucleotide). For example, antibodies can be bound (e.g., by direct physical adsorption) to the conductive polymer of the particulate composition by incubating the antibodies in a buffer (e.g., a phosphate buffer at a pH of about 7.4 containing dimethylformamide and lithium chloride) suspension of the particulate composition. Alternatively, the particulate composition can be first incubated in the presence of a suitable linker (e.g., glutaraldehyde) followed by incubation of the linker-functionalized particulate composition with the antibodies to bind the antibodies thereto (e.g., glutaraldehyde can form a link between the antibodies and the particulate composition, such as the conductive polymer component thereof). For example, an immunoglobulin with an Fc region and an antigen-binding region capable of specifically binding to the target analyte (e.g., IgA, IgD, IgE, IgG, IgM, subclasses thereof, and combinations thereof) can be incubated with a immunoglobulin-binding protein having a binding affinity to the Fc region of the immunoglobulin (e.g., a bacterial surface protein such as protein A, protein G, protein A/G, and combinations thereof), such that the immunoglobulin-binding protein binds to the conductive polymer (e.g., via adsorption) and the Fc region of the immunoglobulin, thereby preferentially orienting the resulting immunoconjugate so that the antigen-binding region of the immunoglobulin is outwardly directed relative to the conductive polymer and the magnetic nanoparticle of the particulate composition (e.g., which enhances binding/capture efficiency of the immunoglobulin). Similarly, oligonucleotides can be incubated in a buffer (e.g., an acetate buffer at a pH of about 5.2) suspension of the particulate composition that also includes an immunoconjugating agent (e.g., 1-ethyl-3-(3-dimethylaminopropyl) carbodiimide hydrochloride ("EDAC")). After a suitable incubation period (i.e., depending on the rate of binding between the binding pair member and the conductive polymer) the resulting biologically enhanced nanoparticles can be blocked, washed, centrifuged, and then stored as a suspension (e.g., in aqueous LiCl for an antibody on a phosphate-buffered saline ("PBS") solution for an oligonucleotide).

Biosensor

The detection system for capturing and identifying a target analyte in a sample can include a biosensor device incorporating a magnet for analyte conjugate/triplex immobilization. As illustrated in FIGS. 1E and 1F, the biosensor 100 can include a magnet 130 positioned below the immobilization surface 110 of the biosensor 100. When the analyte conjugate 300, 310 includes a magnetic moiety (e.g., separate from or combined with the conductive polymer label), application of a magnetic field with the magnet 130 immobilizes the conjugate 300, 310 and pulls it tightly against the immobilization surface 110 to enhance a subsequent conductimetric or electrochemical measurement.

FIGS. 1E and 1F illustrate a suitable biosensor 100 (e.g., a screen-printed carbon electrode (SPCE) as shown) for detection of the analyte conjugate 300, 310. The illustrated biosensor 100 includes a working electrode 110 as a detection surface and a counter/reference electrode 120, which electrodes can be used for voltage/current application and conjugate 300, 310 detection. The magnet 130 is mounted below the detection surface 110 (on or adjacent a bottom surface thereof opposing a corresponding top surface for conjugate 300, 310 application) for immobilization of the conjugate 300, 310. The magnet 130 can be a permanent magnet or an (electro) magnet selectable between ON and OFF states in which a magnetic field is generated or not generated.

The specific type of biosensor is not particularly limited and generally includes devices known and used for the detection of an analyte by combining a biological component (e.g., biological material such as tissue, microorganisms, organelles, cell receptors, enzymes, antibodies, nucleic acids, probe DNA, biomimic, etc.) with a physicochemical transducer element (e.g., an element that works in a physicochemical way; optical, electrical, piezoelectric, electrochemical, etc.) that transforms the signal resulting from the interaction of the analyte with the biological element into another signal (i.e., transducers) that can be measured and quantified. In some embodiments, the transducers act as a means for amplifying a low number or low concentration of analytes in a sample into a detectable and repeatable (meaningful) signal.

As described above, the analyte conjugate 300, 310 can be detected once immobilized on an electrode surface of a SPCE biosensor 100. Any suitable biosensor platform may be used, however. For example, a sample containing the conjugate 300, 310 can be applied to a capture region of a lateral flow assay device, where the capture region includes a means for immobilizing the conjugate 300, 310 (e.g., a magnet mounted thereunder and/or an adsorbed specific or non-specific binding pair member in the capture region). The sample can be applied to the capture region in a variety of ways, such as by direct addition thereto or by capillary transport of the sample from an application region to the capture region. The presence of the target analyte in the sample can be determined (e.g., and optionally quantified) by magnetically or conductimetrically detecting the analyte conjugate 300, 310 (e.g., by detecting the magnetic nanoparticle or conductive polymer component thereof) in the capture region.

Target Analyte Detection

As generally illustrated in FIGS. 1A-1F and described above, the biosensor 100, the magnetic capture probe 210, the conductive polymer label 220, and/or the combined capture probe/label 240 of any of the above embodiments can be used in an assay to detect the presence of the target analyte 230 in the sample 232 (e.g., which can contain the target analyte 230 of interest as well as non-target components). Specific detection of the target analyte 230 is effected using binding pair members 214, 224 selected to be complementary to the target analyte 230. The probes/labels 210, 220, 240 can be independently provided in a variety of forms, for example a liquid suspension, a powder, or as part of an assay device (e.g., in an application region of a lateral flow assay device).

The probes/labels 210, 220, 240 are contacted with the sample 232 for a time sufficient to bind any target analyte 230 in the sample 232 to the binding pair members 214, 224, thereby forming an analyte conjugate 300, 310. The sample 232 and probes/labels 210, 220, 240 can be contacted in any convenient way, for example by combining the components in a reaction vessel (e.g., together or in series). The contact time required to obtain sufficient binding between the target analyte and the binding pair member generally depends on the kinetics of the particular analyte-binding pair member interaction (e.g., at least 1, 2, 5, or 10 minutes and/or up to 30, 60, 90, or 120 minutes).

A magnetic field can be applied to the sample 232 (e.g., using a magnet 240) to concentrate the analyte conjugate 300, 310 using an immunomagnetic separation process. Specifically, the applied magnetic field attracts the magnetic portion of the analyte conjugate 300, 310, causing individual particles of the conjugate 300, 310 to migrate to and concentrate in a region of the assay reaction vessel. Thus, after migration of the conjugate 300, 310, a portion of the sample 232 that is substantially free from the conjugate 300, 310 can be removed (e.g., by draining, skimming, pipetting, washing, etc.), thereby forming a sample concentrate that contains substantially all of conjugate 300, 310. The sample concentrate can include some free probes/labels 210, 220, 240 that are not conjugated to a target analyte 230.

The analyte conjugate 300, 310 is then applied to the detection surface 110 of the biosensor 100 (e.g., and optionally immobilized thereon as described above). In the illustrated SPCE biosensor 100, the conjugate 300, 310 can be applied directly to the detection surface 110 (e.g., by pipetting a liquid suspension of the conjugate 300, 310, such as that resulting from an immunomagnetic separation process). Prior to detection of the analyte conjugate 300, 310 (e.g., via the conductive polymer component thereof), the analyte conjugate 300, 310 is suitable electrically re-activated and the detection surface 110 having the triplex 300 immobilized thereon is suitably washed (e.g., by rinsing with DI water or other suitable wash fluid such as one containing an electrically activating acid dopant). Washing can be performed during the application of a magnetic field via the magnet 130 to remove non-magnetically attractable components/conjugates from the biosensor 100 detection surface 110. Washing enhances the qualitative and quantitative accuracy of the assay, because it provides a means to eliminate free probes and/or labels 210, 220, 240 on the detection surface 110 that are not bound to any target analyte 230 (but which could otherwise be detectable and contribute to a false positive or positively biased concentration due to the presence of the conductive polymer).

The biosensor 100 is then used to detect the presence of the immobilized analyte conjugate 300, 310, such as via the conductive polymer component thereof. A positive identification of the conjugate 300, 310 in the sample (concentrate) applied to the detection surface 110 indicates the presence of the target analyte 230 in the original sample 232. If a quantitative determination of the conjugate 300, 310 is made, any dilution and concentration factors can be used to determine the concentration of the target analyte 230 in the original sample 232. The specific method of detection of the analyte-nanoparticle complex is not particularly limiting, and can include methods applicable to immunoassays in general or immunomagnetic assays in particular (e.g., agglomeration, spectrophotometric detection, colorimetric detection, radioactive detection, visual inspection). In the method illustrated in the figures and examples, the electrically conductive polymer component of the conjugate 300, 310 can be conductimetrically or electrochemically detected (e.g., by conducting cyclic voltammetry to detect the conductive polymer moiety of the electrically activated analyte conjugate 300, 310).

Kit

The disclosed compositions also can be provided in a kit. A suitable kit includes one or more of a probe/label 210, 220, 240 specific to a desired target analyte 230 (optionally) and a biosensor 100 (e.g., including the magnet 130 for immobilization). In an embodiment, the kit can be intended to be used for multiplexed analysis of several different target analytes 230 such that it contains a plurality of different probe/label pairs 210, 220, 240 where each analyte probe/label pair 210, 220, 240 has specific binding pair members 214, 224 capable of specifically binding to a different target analyte 230. The kit can include one or a plurality of biosensors 100. The kit can generally include a variety of other optional components that may be desired and/or appropriate, for example a reaction vessel (e.g., a container for mixing the probes/labels 210, 220, 240 and a sample 232 to be analyzed), a magnet, wash reagents, detector reagents, positive and/or negative control reagents, assay kit instructions according to any of the methods disclosed herein, and other additives (e.g., stabilizers, buffers). The relative amounts of the various reagents may be varied widely, to provide for concentrations in solution of the reagents that substantially optimize the sensitivity of the assay. Particularly, the reagents may be provided as dry powders (e.g., lyophilized) which on dissolution will provide for a reagent solution having the appropriate concentrations for combining with the sample 232.

EXAMPLE

The following example illustrates various compositions, apparatus, and methods according to the disclosure for detecting target analytes such as bacterial pathogens, but are not intended to limit the scope of the claims appended hereto.

In this example, E. coli O157:H7 cells are isolated via immunomagnetic separation (IMS) and labeled with biofunctionalized electroactive polyaniline (immuno-PANI). Labeled cell complexes are deposited onto a disposable screen-printed carbon electrode (SPCE) sensor and pulled to the electrode surface by an external magnetic field, to amplify the electrochemical signal generated by the polyaniline. Cyclic voltammetry is used to detect polyaniline and signal magnitude indicates the presence or absence of E. coli O157:H7. As few as 7 CFU of E. coli O157:H7 (corresponding to an original concentration of 70 CFU/ml) were successfully detected on the SPCE sensor. The assay requires 70 min from sampling to detection, giving it a major advantage over standard culture methods in applications requiring high-throughput screening of samples and rapid results. The method can be performed with portable, handheld instrumentation and no biological modification of the sensor surface is required.

Experimental

Reagents and Materials:

Aniline monomer, hydrochloric acid (HCl), sodium dodecyl sulfate (SDS), ammonium persulfate, and methanol were used for the synthesis of polyaniline. Polysorbate-20 (TWEEN-20), TRITON X-100, phosphate buffered saline (PBS), trizma base, casein, and sodium phosphate were used in immunomagnetic separation and polyaniline labeling of bacteria. All of the above reagents were purchased from Sigma-Aldrich (St. Louis, Mo.) except SDS, which was purchased from Pierce/Thermo Scientific (Rockford, Ill.).

Monoclonal anti-E. coli O157: H7 antibodies were obtained from Meridian Life Science, Inc. (Saco, Me.). DYNABEADS MAX E. coli O157 immunomagnetic beads were purchased from Invitrogen Life Science. A strain of E. coli O157:H7 was obtained from the NanoBiosensors Laboratory collection at Michigan State University, and grown in tryptic soy broth (BD Biosciences, MD) at 37° C. for 24 h. Viable cells were enumerated by microbial plating (20 h incubation at 37° C.) on TSA 11 trypticase soy agar, modified (BD Biosciences, MD).

All the solutions and buffers used in this example were prepared in de-ionized (DI) water from Millipore DIRECT-Q system, as follows: phosphate buffered saline (10 mM PBS, pH 7.4), phosphate buffer (100 mM phosphate buffer, pH 7.4), blocking buffer (100 mM Tris-HCl buffer, pH 7.6, with 0.1% (w/v) casein). Magnetic separations were performed with a commercial magnetic separator (FLEX-IMAG, from SpheroTech Inc., IL). Centrifugation was performed with an Eppendorf 5415 R microcentrifuge. Hybridization of biological materials was carried out at room temperature with rotation on a tube rotisserie (LABQUAKE, Thermo Scientific, MA).

Detection Apparatus:

Cyclic voltammetric measurements were performed with a potentiostat/galvanostat connected to a personal computer. A PalmSens handheld potentiostat with PSLITE software (PalmSens, Houten, Netherlands), and a VersaStat II potentiostat with POWERCV software (Princeton Applied Research, MA) were used. Screen-printed carbon electrode (SPCE; FIG. 1F) sensors (Gwent Inc., UK) consist of a carbon/graphite working electrode (diameter 4 mm) and a silver/silver chloride counter/reference electrode. Every SPCE sensor was rinsed with sterile DI water and allowed to dry before test solution was applied. Sensors were disposed of after single use.

Preparation and Characterization of Polyaniline Nanostructures:

Polyaniline nanostructures (nano-PANI) were synthesized by chemical oxidative polymerization in micellar solution. Briefly, 0.043 M aniline monomer was dispersed in 0.1 M HCl containing approximately 0.2 M SDS. Ammonium persulfate (APS) dissolved in 0.1 M HCl was added dropwise, such that aniline:APS ratio=2. The solution was stirred at room temperature for 90 min and changed from colorless to dark green, indicating formation of conductive polyaniline emeraldine salt. Methanol was added to quench polymerization. Polyaniline precipitate was collected by centrifugation, washed in 50% methanol, and finally suspended in phosphate buffer containing 0.05% TRITON X-100. Very brief (1-2 s) centrifugation was performed to precipitate only the largest polyaniline particulates. The supernatant, consisting of bright green, well-dispersed polyaniline nanostructures, was reserved and used for further experiments. The size and morphology of the nano-PANI were characterized using a 200 kV field emission transmission electron microscope (JEOL 2200 FS). The electrical conductivity of nano-PANI in solution was measured using an ACCUMET BASIC AB30 conductivity meter (Fisher Scientific).

Magnetic Capture of Bacterial Target:

*E. coli* O157:H7 in pure culture was serially diluted in PBS. Commercial immunomagnetic beads (IMBs), pre-coated with antibody to *E. coli* O157, were combined with the diluted bacteria (20 µl beads per 1 ml dilution) and hybridized for 10 min. IMB-*E. coli* complexes were magnetically separated from unbound cells, washed once in PBS containing 0.05% Tween-20, and resuspended in PBS. IMB-based capture of *E. coli* O157: H7 from a complex sample matrix is depicted in FIG. 1A.

Polyaniline Labeling of Magnetically Captured Target:

Monoclonal anti-*E. coli* O157:H7 antibodies were coated onto nano-PANI by direct physical adsorption. Antibodies (0.1 mg/ml, final concentration) were added to nano-PANI suspended in phosphate buffer containing 0.05% TRITON X-100, and hybridized for 1 h. Following adsorption of antibody, the bio-modified polyaniline (immunoPANI) was centrifuged (3 min at 10,000 rpm) to remove unbound antibodies, washed twice with blocking buffer (0.1% (w/v) casein to block unoccupied reactive sites on polyaniline), and finally resuspended in phosphate buffer containing 0.05% TRITON X-100, and stored at 4° C. A Shimadzu UV-3101 PC spectrophotometer was used to compare protein content (absorbance at 280 nm) of the antibody solution before and after incubation with nano-PANI, in order to confirm hybridization between antibodies and nano-PANI.

Immuno-PANI was added to the immunomagnetically captured *E. coli* O157:H7 (IMB-*E. coli*) solutions at 10% (v/v), and hybridized for 30 min. IMB-*E. coli*-immuno-PANI complexes were magnetically separated from unbound immuno-PANI, washed twice in PBS containing 0.05% TRITON X-100, and finally resuspended in PBS. Polyaniline labeling of immunomagnetically captured *E. coli* O157:H7 cells is depicted in FIG. 1A.

Electrochemical Detection of Polyaniline-Labeled Target:

The IMB-*E. coli*-Immuno-PANI complexes were magnetically separated and suspended in 0.1 M HCl for 10 min in order to electrically activate the polyaniline by acid doping. The volume of acid in which complexes were suspended was half of the original solution volume, so that the concentration of IMB-*E. coli*-immuno-PANI complexes was doubled prior to detection. Immediately following the incubation period, a volume of 100 µl of IMB-*E. coli*-immunoPANI in 0.1 M HCl was added to the sample well of the SPCE sensor, and the sensor was placed on a magnetic field in order to attract and position the complexes tightly onto the sensor surface (FIGS. 1A and 1E), to amplify the electrochemical signal generated by the polyaniline. The SPCE sensor was connected to the potentiostat/galvanostat, and a voltammetric cycle between +1.0 V and −0.4V was applied at a scan rate of 100 mV/s. Each sensor was scanned with four complete, consecutive cycles, and for each cycle the response current data was recorded.

Results

Immunomagnetic Capture and Polyaniline Labeling of Bacterial Target:

Successful immunomagnetic extraction of *E. coli* O157:H7 was confirmed by microbial plating of the IMB-*E. coli*-immuno-PANI solutions. Percent capture efficiency was calculated as (captured viable cell concentration/original viable cell concentration)×100. The concentration of captured viable cells (CFU/ml) was also used to estimate the actual number of cells present in the 100-µl sample which was deposited onto the SPCE. For four different concentrations of *E. coli* O157:H7 (blank, $10^1$, $10^3$, and $10^5$ CFU/ml), Table 1 shows the original and captured cell concentrations, the capture efficiency, the absolute number of cells present on the SPCE during detection, and the minimum electrical current signal obtained during detection. Reported values are the mean of three identical trials±one standard deviation.

TABLE 1

Original and captured cell concentrations, capture efficiencies, estimated cell numbers on SPCE sensor for detection, and electrical current signals

| Original viable cell concentration (CFU/ml) | Mean captured viable cell concentration (CFU/ml) ± S.D. (n = 3) | Capture efficiency (%) | Mean viable cell number (CFU) on SPCE ± S.D. (n = 3) | Mean minimum current signal (µA) ± S.D. (n = 3) |
|---|---|---|---|---|
| 0 (Blank) | 0 | — | 0 | −2.8 ± 0.75 |
| $7.1 \times 10^1$ | $(3.3 \pm 0.2) \times 10^1$ | 47.2 ± 32.7 | $(7.0 \pm 5.0) \times 10^0$ | −5.0 ± 0.40 |
| $7.1 \times 10^3$ | $(3.0 \pm 0.2) \times 10^3$ | 42.3 ± 3.3 | $(6.0 \pm 0.5) \times 10^2$ | −6.1 ± 1.1 |
| $7.1 \times 10^5$ | $(3.4 \pm 0.6) \times 10^5$ | 48.3 ± 8.7 | $(6.8 \pm 1.2) \times 10^4$ | −7.4 ± 0.42 |

The capture efficiencies attained (40-50%) are comparable to other published bacterial capture studies using this brand of commercial IMBs. The minimum current signals displayed in the last column of Table 1 demonstrate that the electrochemical detection results agree with microbial plating results (increasing cell concentration corresponds to increasing absolute value of current signal).

Nano-PANI, investigated by transmission electron microscopy, consists of spherical particles less than 50 nm in diameter and clusters of particles ranging in size from approximately 100 to 300 nm. The nano-PANI solution is a bright green color, indicating that it is the conductive emeraldine salt form of polyaniline, which results from the acid-doping polymerization method employed here. Polyaniline has well-characterized pH-induced redox reversibility, meaning that in neutral or basic conditions, loss of electroactivity will occur. The electrical conductivities of nano-PANI suspended in DI water and in 0.1 M HCl were determined to be 0.4 mS/cm and 26.4 mS/cm, respectively. Both solutions contained 0.1% (v/v) TRITON X-100 to keep nano-PANI well dispersed during measurement. The conductivity of nano-PANI is significantly increased in the presence of hydrochloric acid as a dopant (relative to non-doped nano-PANI in neutral DI water). To ensure maximum electroactivity of the polyaniline label used in this assay, the IMB-$E.$ $coli$-immuno-PANI complexes were re-doped in 0.1 M HCl for 10 min immediately prior to electrochemical detection.

Immunofunctionalization of nano-PANI was carried out by physical adsorption of antibodies onto the polyaniline surface. Electrostatic interactions between the negatively charged Fc portion of the antibodies and the positively charged polymer are thought to play a role in adsorption and orientation of the biomolecules. Successful conjugation of antibodies onto nano-PANI was confirmed by measuring the absorbance of the antibody solution at 280 nm, an indicator of protein content. The measured absorbance of the conjugation supernatant was lower than that of the original antibody solution, demonstrating that antibodies were retained on the nano-PANI during hybridization.

Figure 2:
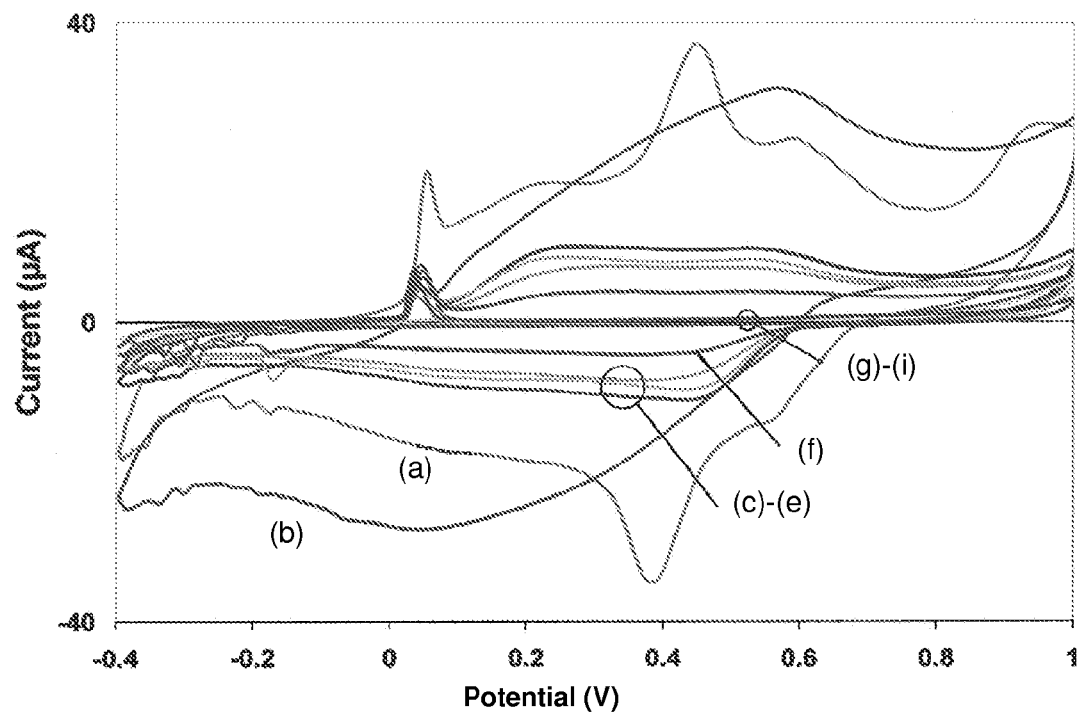
FIG. 2 is a graph illustrating cyclic voltammograms of samples suspended in 0.1 M HCl: (a) nano-PANi, (b) immuno-PANi, (c) IMB-*E. coli*-immuno-PANi, $7 \times 10^4$ CFU, (d) IMB-*E. coli*-immuno-PANi, $6 \times 10^2$ CFU, (e) IMB-*E. coli*-immuno-PANi, 7 CFU, (f) IMB-No *E. coli*-immuno-PANi (blank test), (g) IMBs, (h) *E. coli*, $10^5$ CFU, (i) 0.1 M HCl alone. Scan rate 100 mV/s. Voltammograms were obtained in the fourth voltammetric scan performed.

Electrochemical Detection of Polyaniline-Labeled Target:

From each electrochemical test, cyclic voltammograms (plot of response current vs. applied potential) were recorded for each of the four consecutive scans performed. FIG. 2 depicts cyclic voltammograms of nano-PANI, immuno-PANI, and IMB-$E.$ $coli$ immuno-PANI solutions containing various bacterial counts. Also shown are voltammograms of IMBs, $E.$ $coli$ O157:H7 cells, and 0.1 M HCl solution alone, at concentrations equivalent to those used in the IMB-$E.$ $coli$-immuno-PANI assay.

FIG. 2 curve (a), the cyclic voltammogram of nano-PANI, shows three oxidation peaks (having positive current values) and three corresponding reduction peaks (having negative current values), which are characteristic of conducting polyaniline. Oxidation peaks occur at approximately 0.25, 0.45, and 0.6 V. The first of these peaks represents the initial step in oxidation of reduced-form polyaniline (leucoemeraldine to protoemeraldine/emeraldine), the second represents the presence of soluble species arising from degradation of polyaniline, and the third peak represents the final step in oxidation of polyaniline (emeraldine to nigraniline/pernigraniline). The fourth cathodic peak, occurring at 0.95 V, is not typically found in cyclic voltammograms of pure polyaniline, and may be associated with the surfactant (SDS) which was incorporated into the nano-PANI during synthesis. Reduction peaks occur at approximately 0.1, 0.4, and 0.5 V. The oxidation and reduction potentials of polyaniline will vary with scan rate (in this case 100 mV/s) and with the type and concentration of dopant acid (in this case HCl at 0.1 M).

Immunofunctionalization of nano-PANI masks its electroactivity to some extent, as shown by the smaller magnitude and loss of peak resolution in the cyclic voltammogram of immuno-PANI, curve (b). Specifically, the second and third oxidation (and corresponding reduction) peaks merge into one, and overall peak height decreases. Curves (c-e) are the IMB-$E.$ $coli$-immuno-PANI complexes, with bacteria counts ranging from $7 \times 10^4$ to $7 \times 10^0$ CFU. These curves exhibit the same shape as that of immuno-PANI, but are smaller in magnitude because excess immuno-PANI has been removed by washing, and only that which is bound to $E.$ $coli$ O157:H7 cells remains. Curve (f), the blank test, has a similar shape but significantly lower magnitude. The low level of immuno-PANI present in the blank test is due to non-specific interaction with IMBs, which prevents some of the immuno-PANI from being removed during washings. This is considered as the background signal. The fact that the tests containing $E.$ $coli$ cells (curves c-e) have significantly higher magnitude than the background signal demonstrates that immuno-PANI is indeed specifically binding to $E.$ $coli$ O157:H7 cells. The remaining curves (g-i) have very low current magnitude and no polyaniline peaks, demonstrating that HCl, IMBs, and $E.$ $coli$ O157:H7 cells alone do not significantly contribute to the magnitude of the signal. The narrow spike occurring around 0.05 V arises from the HCl solution in which all the samples are suspended.

For simplicity of comparison, each cyclic voltammogram (plot of response current vs. applied potential) can be represented by a single numeric parameter. Three parameters were evaluated for each voltammogram: the quantity of charge transferred ($\Delta Q$), the maximum current value, and the minimum current value. Charge transfer $\Delta Q$ is computed as the integral of the current with respect to time. Maximum current is taken as the positive current value occurring at +0.245 V on the cyclic voltammogram (approximate location of the highest oxidation peak). Minimum current is taken as the negative current value occurring at +0.420 V on the cyclic voltammogram (approximate location of the lowest reduction peak).

Figure 3:
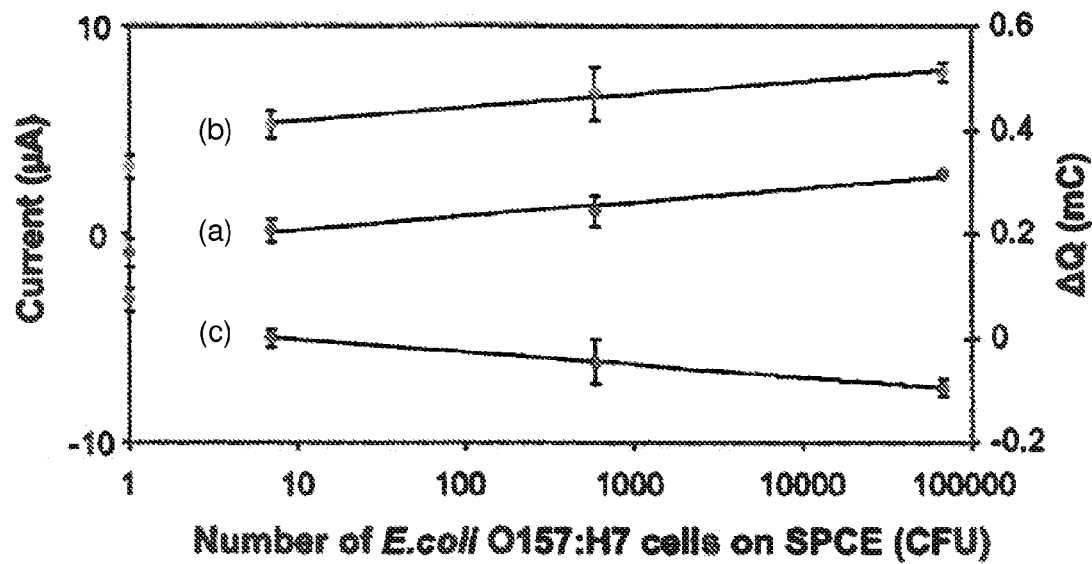
FIG. 3 is a graph illustrating the average $\Delta Q$ (a; $y=0.0118$ $\ln(x)+0.179$; $R^2=0.9699$), average maximum current (b; $y=0.274$ $\ln(x)+4.81$; $R^2=0.9844$), and average minimum current (c; $y=-0.260$ $\ln(x)-4.47$; $R^2=0.9998$) values obtained in cyclic voltammetry of IMB-*E. coli*-immuno-PANi solutions with cell counts ranging from 7 CFU to $7 \times 10^4$ CFU. Error bars represent±one standard deviation (n=3). Data was obtained in the first voltammetric scan performed.

FIG. 3 displays the charge transfer values and the maximum and minimum current values obtained from the cyclic voltammograms of test solutions containing 0, $7 \times 10^0$, $6 \times 10^2$, and $7 \times 10^4$ CFU. Values shown are the mean of three replicate trials, and error bars represent±1 standard deviation. All the data was collected in a single experiment. Two values, confirmed to be outliers with 95% confidence by a two-sided Grubbs' test, were excluded from the data set. The outliers occurred in tests containing $10^2$ or $10^4$ CFU $E.$ $coli$ O157:H7, and were exceptionally high values. Thus even the outlying values were not false negatives (which would be particularly undesirable for food and water safety applications), but only "extreme positive" results, obtained for samples which were indeed positive.

All the three sensor response parameters ($\Delta Q$, maximum current, and minimum current) are strongly linear across the three cell concentrations tested. Each of the regression coefficients ($R^2$) are greater than 0.96. Logarithmic regression equations are displayed in the figure. A single-factor ANOVA test indicated that the $\Delta Q$ values obtained for each cell count ($7 \times 10^4$, $6 \times 10^2$, $7 \times 10^0$, and 0 CFU) are statistically different from one another with 99% confidence. The same result was obtained for maximum and minimum current values.

Figure 4:
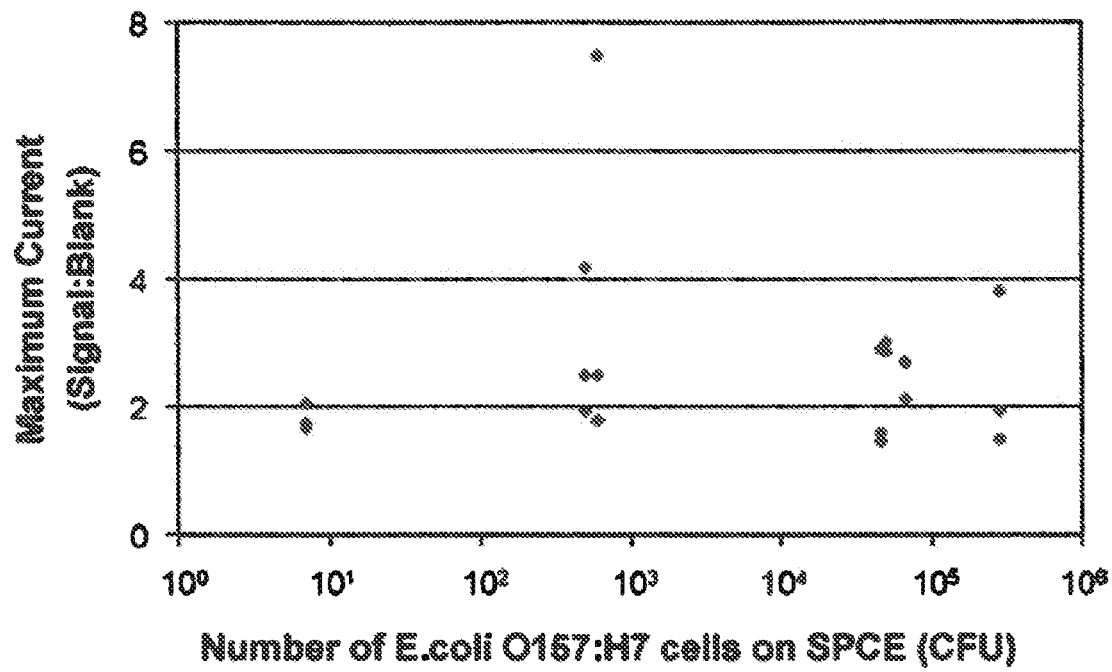
FIG. 4 is a plot of the maximum current signal:blank ratios of IMB-*E. coli*-immuno-PANi solutions with cell counts ranging from 7 CFU to $3 \times 10^5$ CFU. Data was obtained in the fourth voltammetric scan performed.

FIG. 4 depicts the maximum current signal:blank ratios from 20 positive tests carried out in four different experiments, with cell counts ranging from $7 \times 10^0$ to $3 \times 10^5$ CFU. Signal:blank ratios were obtained by dividing the maximum current value of each positive test by the average maximum current value of the blank tests which were performed on the same day. Signal:blank ratios were used because absolute signal values vary from one experiment to the next. This day to day variation in signal magnitude may be attributable to the following causes: (1) the electroactivity of polyaniline is temperature dependent, and (2) batch-to-batch variation in nano-PANI synthesis and immuno-PANI preparation will alter the quality and quantity of polyaniline in test solutions.

The strong linear trend observed in FIG. 3, in which all the data was collected in a single experiment, indicates a linear dynamic range of $7\times10^0$ to $7\times10^4$ CFU ($7\times10^1$ to $7\times10^5$ CFU/ml). However, the linearity of the sensor response disappears when data from several different experiments are pooled (FIG. 4). Without linearity, the sensor is still useful in providing a qualitative (positive/negative) result. If quantitative results are desired, a new calibration curve must be constructed for each experiment in which unknown samples are tested. Even so, the biosensor's strong linearity and wide linear range (within one experiment) is an advantage, showing that it has the potential to be developed into a fully quantitative detection method, if day to day variation in signal values can be reduced. FIG. 4 demonstrates that the biosensor results are reproducible for qualitative (yes/no) detection, because all the 20 positive tests produced signals much higher than the blank tests (signal:blank ratio≥1.45).

The data displayed in FIGS. 3 and 4 indicate that as few as 7 CFU of E. coli O157:H7 present on the SPCE sensor (corresponding to an original cell concentration of 70 CFU/ml) can be detected with signal:blank ratio >1.5 (the signal:blank ratios at this cell count are 1.67, 1.74, and 2.05). Slightly lower signal:blank ratios are observed at higher cell counts (1.45 and 1.50 at $4.7\times10^4$ and $2.9\times10^5$ CFU, respectively) which may indicate a slight Hooke effect. It is important to note, though, that for four of the positive tests, signal:blank ratios were greater than 3, and even as high as 7.5. Future efforts will focus on improving the sensitivity of the sensor until signal:blank ratios greater than 3 can be consistently achieved for all the positive samples.

Prior to detection, the IMB-E. coli-immuno-PANI complexes were immunomagnetically separated and resuspended in half of the original volume, in order to double the concentration being applied to the SPCE sensor. This resulted in a larger amount of PANI on the sensor, and consequently a stronger electrochemical signal as compared to unconcentrated test solutions (data not shown). A potential way to increase the sensitivity of the system is to use larger sample volumes and immunomagnetically concentrate the test solutions by more than twofold before they are applied to the SPCE sensor.

Figure 5:
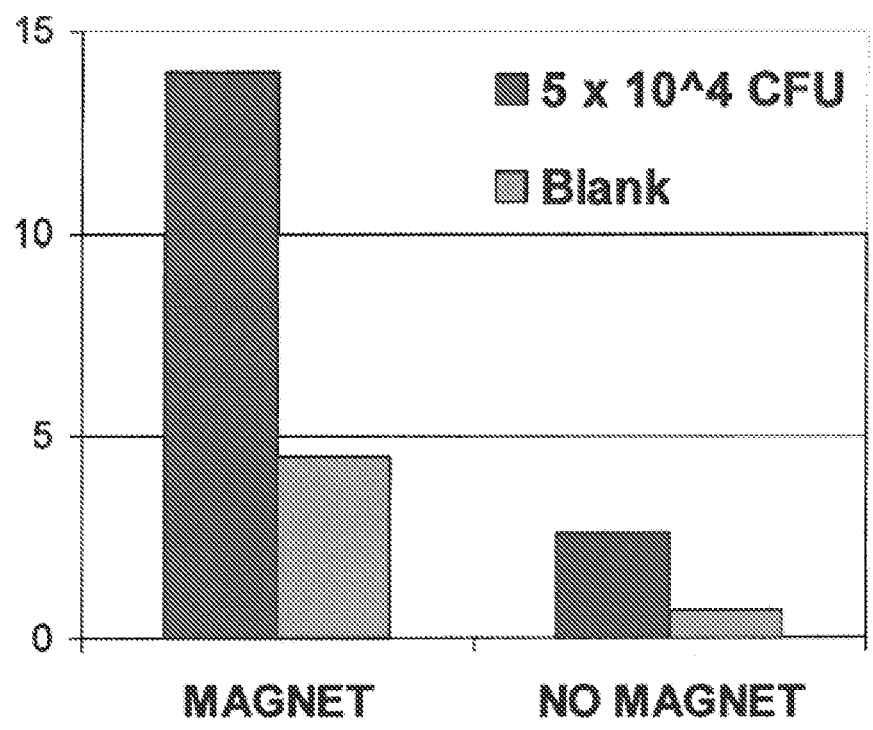
FIG. 5 is a graph illustrating the absolute current (μA) at 0.45 V in IMB-*E. coli*-immuno-PANi solutions at 0 (blank) and $5 \times 10^4$ CFU.

Also prior to detection, an external magnetic field was used to draw IMB-E. coli-immuno-PANI complexes to the sensor surface (FIG. 1A), where the electric field is most concentrated. Magnetically positioning the polyaniline as near as possible to the electrode is a simple way of amplifying the electrochemical signal. The presence of the magnetic field results in current values approximately five times higher than those obtained without the magnetic field. Additionally, the signal:blank ratio is slightly higher in the presence of the magnetic field than in its absence (FIG. 5).

The biosensor's limit of detection (7 CFU or 70 CFU/ml) is lower than the infectious dose of E. coli O157:H7 (10-100 cells), making it a practical detection method. Table 2 compares this with other biosensors for E. coli O157:H7 which also employ IMS and some type of electrochemical detection. The detection limit of the biosensor is one order of magnitude lower than any of the detection limits of the similar methods found in the literature, giving this biosensor a clear advantage.

TABLE 2

Comparison of the analytical performance of several biosensors which employ IMS and electrochemical techniques to detect E. coli O157:H7 cells from pure culture

| Biosensor principle | Detection limit | Linear range | Assay time |
| --- | --- | --- | --- |
| IMS, label-free amperometric detection | $10^5$ CFU/ml | $10^6$ to $10^8$ CFU/ml | 120 min |
| IMS, enzymatic label and amperometric detection | $6 \times 10^2$ CFU/ml | Nonlinear | 120 min |
| IMS, enzymatic label and square wave voltammetry detection | $5 \times 10^3$ CFU/ml | $10^3$ to $10^6$ CFU/ml | 80 min |
| IMS, label-free electrochemical impedance spectroscopy detection | $8 \times 10^5$ CFU/ml ($1.6 \times 10^2$ CFU) | Nonlinear | 35 min |
| IMS, conducting polymer label and cyclic voltammetry detection | $7 \times 10^1$ CFU/ml ($7 \times 10^0$ CFU) | $10^1$ to $10^5$ CFU/ml | 70 min |

The linear range of $7\times10^1$ to $7\times10^5$ CFU/ml observed for this biosensor (in data from a single experiment, FIG. 3) is also an advantage. As shown in Table 2, other IMS-electrochemical detection methods are either not linear at all or have a smaller linear range (≤3 orders of magnitude) than that of the example sensor (4 orders of magnitude).

The FDA reports that the standard method can detect E. coli O157:H7 at <1 CFU/g of food. Since the biosensor in this example can detect as few as 7 CFU, it should also be able to detect the pathogen at <1 CFU/g in a typical food sample (≥25 g). The time required to carry out the biosensor assay (from sampling to detection) is approximately 75 min. This is a huge advantage over the standard (culture) method, which requires 24 h even for an initial positive/negative result. Also, this assay time is competitive in comparison with other IMS electrochemical detection sensors (Table 2), with assay times ranging from 35 min to 2 h. The biosensor would be ideal for high throughput initial screening of samples, after which any positive results could be confirmed by standard methods. Another important advantage of this biosensor is its portability. The handheld potentiostat can be paired with a pocket PC, battery-operated, and transported easily. The SPCE sensors require no chemical or biological modification of the electrode surface, and therefore can be stored up to a year. All the other necessary equipment and reagents can also be transported and operated remotely, which enables the possibility of field-based testing with this biosensor.

SUMMARY

This example illustrates a rapid electrochemical method for E. coli O157:H7 detection. Cells are isolated by immunomagnetic separation, labeled with electroactive polyaniline, and detected by cyclic voltammetry on screen-printed carbon electrodes. Results show a detection limit of 7 CFU (70 CFU/ml), with a linear range of $10^1$ to $10^5$ CFU/ml. The assay requires 70 min from sampling to result. The low detection limit and short assay time give this biosensor the potential to replace time-consuming culture methods as the means of initial screening for rapid qualitative results. Another major advantage of the biosensor is its portability. No surface modification of the SPCE sensor is required, making it stable for long term storage and transport. A handheld, battery-powered potentiostat and pocket PC make it feasible to perform this assay in the field. The biosensor could be adapted for other targets simply by use of different antibodies, and immunomagnetic separation of the target can be performed in a variety of sample matrices.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clarity of understanding only, and no unnecessary limitations should be understood therefrom, as modifications within the scope of the disclosure may be apparent to those having ordinary skill in the art.

Throughout the specification, where the compositions, kits, processes, or apparatus are described as including components, steps, or materials, it is contemplated that the compositions, kits, processes, or apparatus can also comprise, consist essentially of, or consist of, any combination of the recited components or materials, unless described otherwise. Component concentrations expressed as a percent are weight-percent (% w/w), unless otherwise noted. Numerical values and ranges can represent the value/range as stated or an approximate value/range (e.g., modified by the term "about"). Combinations of components are contemplated to include homogeneous and/or heterogeneous mixtures, as would be understood by a person of ordinary skill in the art in view of the foregoing disclosure.

What is claimed is:

1. A system for binding a target analyte, the system comprising:
   (a) a magnetic nanoparticle capture composition comprising: (i) a magnetic nanoparticle; and (ii) a first binding pair member bound to the magnetic nanoparticle, the first binding pair member being capable of specifically binding to the target analyte; and
   (b) a conductive polymer nanoparticle label composition comprising: (i) a conductive polymer nanoparticle, and (ii) a second binding pair member bound to the conductive polymer nanoparticle, the second binding pair member being capable of specifically binding to the target analyte.

2. The system of claim 1, further comprising:
   (c) a biosensor comprising a detection surface having opposing top and bottom surfaces; and
   (d) a magnetic means for generating a magnetic field positioned adjacent the bottom surface of the detection surface.

3. The system of claim 2, wherein the biosensor is a screen-printed carbon electrode (SPCE), and the detection surface is a working electrode of the SPCE.

4. The system of claim 1, wherein:
   (i) the magnetic nanoparticles comprise at least one of Fe(II) and Fe(III); and,
   (ii) the conductive polymer is selected from the group consisting of polyanilines, polypyrroles, polythiophenes, derivatives thereof, combinations thereof, blends thereof with other polymers, and copolymers of the monomers thereof.

5. A target analyte triplex comprising:
   (a) a magnetic nanoparticle capture composition comprising: (i) a magnetic nanoparticle; and (ii) a first binding pair member bound to the magnetic nanoparticle, the first binding pair member being capable of specifically binding to the target analyte;
   (b) a conductive polymer nanoparticle label composition comprising: (i) a conductive polymer nanoparticle, and (ii) a second binding pair member bound to the conductive polymer nanoparticle, the second binding pair member being capable of specifically binding to the target analyte; and
   (c) the target analyte bound to both the first binding pair member and the second binding pair member.

6. The triplex of claim 5, wherein:
   (i) the magnetic nanoparticles comprise at least one of Fe(II) and Fe(III); and,
   (ii) the conductive polymer is selected from the group consisting of polyanilines, polypyrroles, polythiophenes, derivatives thereof, combinations thereof, blends thereof with other polymers, and copolymers of the monomers thereof.

7. The system of claim 1, wherein the conductive polymer comprises a polyaniline.

8. The system of claim 1, wherein the first binding pair member comprises a first antibody, and the second binding pair member comprises a second antibody.

9. The system of claim 1, wherein the first binding pair member comprises a first oligonucleotide, and the second binding pair member comprises a second oligonucleotide.

10. The system of claim 1, wherein the target analyte comprises a bacterium.

11. The system of claim 1, wherein the target analyte comprises a virus.

12. The system of claim 2, wherein the biosensor comprises a binding pair member capable of specific or nonspecific binding to the target analyte, the binding pair member being immobilized on the detection surface.

13. The triplex of claim 5, wherein the conductive polymer comprises a polyaniline.

14. The triplex of claim 5, wherein the first binding pair member comprises a first antibody, and the second binding pair member comprises a second antibody.

15. The triplex of claim 5, wherein the first binding pair member comprises a first oligonucleotide, and the second binding pair member comprises a second oligonucleotide.

16. The triplex of claim 5, wherein the target analyte comprises a bacterium.

17. The triplex of claim 5, wherein the target analyte comprises a virus.

* * * * *